United States Patent
Bicalho et al.

(10) Patent No.: US 9,533,034 B2
(45) Date of Patent: Jan. 3, 2017

(54) VACCINE FOR INTRAUTERINE DISEASE

(71) Applicant: Cornell University, Ithaca, NY (US)

(72) Inventors: Rodrigo Carvalho Bicalho, Dryden, NY (US); Robert Owen Gilbert, Ithaca, NY (US); Vinicius Machado, Ithaca, NY (US); Marcela Bicalho, Dryden, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/647,623

(22) PCT Filed: Oct. 8, 2013

(86) PCT No.: PCT/US2013/063866
§ 371 (c)(1),
(2) Date: May 27, 2015

(87) PCT Pub. No.: WO2014/084964
PCT Pub. Date: Jun. 5, 2014

(65) Prior Publication Data
US 2015/0335725 A1    Nov. 26, 2015

Related U.S. Application Data

(60) Provisional application No. 61/731,333, filed on Nov. 29, 2012.

(51) Int. Cl.
| | |
|---|---|
| *A61K 39/05* | (2006.01) |
| *A61K 39/114* | (2006.01) |
| *A61J 1/18* | (2006.01) |
| *C12N 1/20* | (2006.01) |
| *A61K 39/108* | (2006.01) |
| *C07K 14/195* | (2006.01) |
| *C07K 14/245* | (2006.01) |
| *A61K 39/00* | (2006.01) |

(52) U.S. Cl.
CPC ............. *A61K 39/114* (2013.01); *A61J 1/18* (2013.01); *A61K 39/0258* (2013.01); *A61K 39/05* (2013.01); *C07K 14/195* (2013.01); *C07K 14/245* (2013.01); *C12N 1/20* (2013.01); *A61K 2039/521* (2013.01); *A61K 2039/54* (2013.01); *A61K 2039/552* (2013.01); *A61K 2039/70* (2013.01)

(58) Field of Classification Search
CPC ..................... A61K 396/0011; A61K 2300/00; A61K 2039/521; A61K 2039/5252; A61K 39/0258; A61K 45/06
See application file for complete search history.

(56) References Cited

U.S. PATENT DOCUMENTS

| | | |
|---|---|---|
| 2002/0054883 A1 | 5/2002 | Nagaraja |
| 2012/0052093 A1 | 3/2012 | Bicalho |

OTHER PUBLICATIONS

Machado, et al., Subcutaneous Immunization with Inactivated Bacterial Components and Purified Protein of *Escherichia coli*, . . . Prevents Puerperal Metritis in Holstein Dairy Cows, PLOS One, vol. 9, No. 3, p. e91734 Mar. 17, 2014.
Santos, et al., Metagenomic analysis of the uterine bacterial microbiota in healthy and metritic postpartum dairy cows, J. Dairy Sci., vol. 94, No. 1, pp. 291-301 Jan. 1, 2011.
Bicalho, M.L.S., et al., Association between virulence factors of *Escherichia coli*, Fustobacterium necrophorum, and Arcanobacterium pyogenes and uterine diseases of dairy cows; Veterinary Microbiology, May 25, 2012, vol. 157, Nos. 1-2, pp. 125-131.
Zastempowska, E., et al., Genotypic characterization and evaluation of an antibiotic resistance of Trueperella pyogenes (Arcanobacterium pyogenes) isolated from milk of dairy cows with clinical mastitis, Veterinary Microbiology, Jul. 20, 2012, vol. 161, No. 1-2, pp. 153-158.

*Primary Examiner* — Padma V Baskar
(74) *Attorney, Agent, or Firm* — Hodgson Russ LLP

(57) ABSTRACT

Provided are compositions and methods for use in prophylaxis of puerperal metritis and improving reproductive function of ruminants. The methods and compositions are for subcutaneous administration and are provided as veterinary compositions and as articles of manufacture. The veterinary composition can contain whole cells selected from whole cells of *Escherichia coli* (*E. coli*), *Trueperella pyogenes* (*T. pyogenes*), *Fusobacterium necrophorum* (*F. necrophorum*) and combinations thereof; and/or proteins selected from *F. necrophorum* leukotoxin (LKT), *E. coli* type 1 fimbrial adhesin (FimH), *T. pyogenes* pyolysin (PLO), and all combinations of the whole cells and the proteins.

2 Claims, 5 Drawing Sheets

VACCINE FOR INTRAUTERINE DISEASE

CROSS-REFERENCE TO RELATED APPLICATIONS

This application claims priority to U.S. Provisional Application No. 61/731,333, filed on Nov. 29, 2012, the disclosure of which is incorporated herein by reference.

FIELD OF THE DISCLOSURE

The present disclosure relates generally to health of ruminants and more specifically to compositions and methods for mitigating the effects of bacterial infections which are related to uterine disease.

BACKGROUND OF THE DISCLOSURE

Postpartum uterine diseases of dairy cows compromise animal welfare and may result in early removal from the herd or impaired reproductive performance. Puerperal metritis is defined by an abnormally enlarged uterus and a fetid, watery, red-brown uterine discharge associated with signs of systemic illness (decreased milk yield, dullness, or other signs of toxemia) and temperature>39.5° C. within 21 d after parturition, while endometritis refers to inflammation of the uterus without systemic illness, happening later than 21 d postpartum. In North America, metritis affects 10% to 20% of cows, whereas the incidence of endometritis is approximately 28%, ranging from 5.3% to 52.6%. Puerperal metritis is commonly treated with antibiotics like penicillin or third-generation cephalosporins. However, antibiotic resistance worldwide is recognized as a top public health challenge and thus there is growing concern regarding the potential impact of extensive use of antibiotics in food animals, including later-generation cephalosporins. The cost of each case of metritis has been reported at approximately US$329-386, due to antibiotic treatment and the detrimental effects of metritis on reproductive performance, milk production, and survivability. Thus, there is an ongoing and unmet need for compositions and methods for use in prophylaxis against uterine diseases. The present disclosure meets these needs.

BRIEF SUMMARY OF THE DISCLOSURE

The present disclosure provides in one aspect a method for prophylaxis of puerperal metritis in a ruminant. The method generally comprises subcutaneously administering a veterinary composition to a ruminant mammal. The veterinary composition can comprise whole cells selected from whole cells of *Escherichia coli* (*E. coli*), *Trueperella pyogenes* (*T. pyogenes*), *Fusobacterium necrophorum* (*F. necrophorum*) and combinations thereof; and/or (2) proteins selected from *F. necrophorum* leukotoxin (LKT), *E. coli* type 1 fimbrial adhesin (FimH), *T. pyogenes* pyolysin (PLO), and all combinations of the whole cells and the proteins. In embodiments, the veterinary composition comprises the whole cells of *E. coli*, *T. pyogenes*, and *F. necrophorum*. In embodiments, the composition comprises the FimH, PLO, and LKT proteins. In embodiments, the veterinary composition comprises the whole cells of *E. coli*, *T. pyogenes*, and *F. necrophorum* and the FimH, PLO, and LKT proteins.

The method is expected to be suitable for use with any ruminant mammal. In embodiments, the ruminant is a member of the genus Bos, such as an ox, cow, or buffalo, and it certain embodiments the ruminant is a dairy cow.

In one approach, the dairy cow is a member of a group of dairy cows and the method includes subcutaneously administering the veterinary composition to additional dairy cows in the group such that the incidence of puerperal metritis in the group is reduced.

In another aspect the disclosure includes improving reproductive function of a ruminant. The method of improving the reproductive function of a ruminant comprises subcutaneously administering to the ruminant a veterinary composition as described herein such that the reproductive function of the ruminant is improved.

In another aspect the disclosure includes a veterinary composition comprising whole cells selected from whole cells of *E. coli*, *T. pyogenes*, *F. necrophorum* and combinations thereof; proteins selected from *F. necrophorum* LKT, *E. coli* FimH, PLO, and combinations thereof; and any combination of the whole cells and the proteins.

In another aspect an article of manufacture is provided. The article of manufacture comprises packaging and at least one sealed container. The container contains a veterinary composition comprising whole cells selected from whole cells of *E. coli*, *T. pyogenes*, *F. necrophorum* and combinations thereof; proteins selected from *F. necrophorum* LKT, *E. coli* FimH, PLO, and combinations thereof; and any combination of the whole cells and the proteins. The packaging further comprises printed material providing an indication that the veterinary composition is for subcutaneous administration to a ruminant for prophylaxis of puerperal metritis, and/or for increasing the reproductive function of the ruminant.

DETAILED DESCRIPTION OF THE DISCLOSURE

Figure 1:
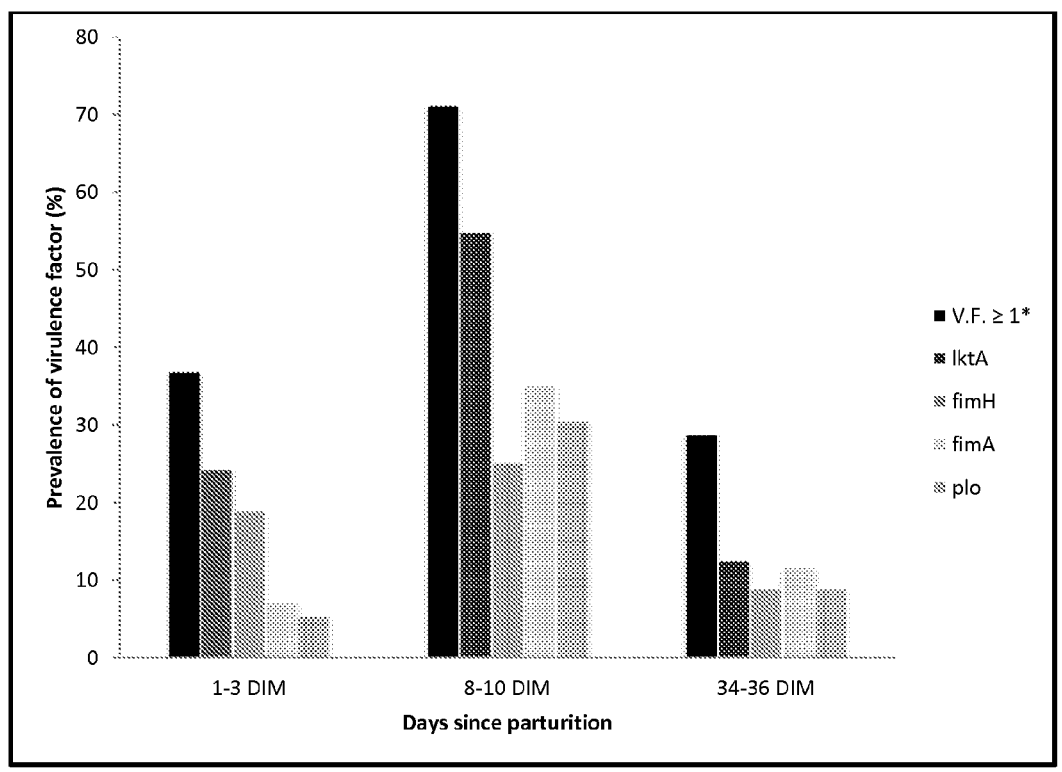
FIG. 1 shows an example of the prevalence of bacterial species-specific virulence factors, lktA (*Fusobacterium necrophorum*), fimH (*Escherichia coli*), and fimA and plo (*Arcanobacterium pyogenes*) at 3 different stages of lactation. *V.F.≥1=At least one virulence factor present.

The present disclosure is generally directed to compositions and methods for improving the health of ruminants, and more specifically to prophylaxis of intrauterine disease of ruminants.

We evaluated several different approaches for developing compositions and methods aimed at mitigating intrauterine diseases in ruminants and evaluated these approaches for a variety of effects on metritis and endometritis, among other responses. As is known in the art, metritis generally involves inflammation of the wall of the uterus, while endometritis generally involves inflammation of the endometrium. Our approaches included making distinct vaccine formulations and evaluating the effects of the different formulations and administration routes on aspects of ruminant health. These effects include stimulation of immunological responses against bacteria and bacterial proteins, effects on endometritis and metritis, effects on intrauterine bacterial contamination, effects on symptoms related to uterine disease, such as rectal temperature, and effects on reproductive function. The results we obtained were unexpected in that we discovered only subcutaneous administration was prophylactic for puerperal metritis, and only subcutaneous administration was effective for improving reproductive function in ruminants. We also determined that intravaginal and subcutaneous vaccination induced a significant increase in serum IgG titers against all antigens, but subcutaneous vaccination was more effective at stimulating IgG production. However, notwithstanding the positive results for prophylaxis of metritis and improvements in reproductive function obtained using subcutaneous administration, none of the vaccines, regardless of route of administration, protected against endometritis or significantly decreased the likelihood of intrauterine bacterial contamination. Thus, as will be more fully described below, the present invention provides novel and effective compositions and methods for prophylaxis of puerperal metritis and for improving reproductive function in ruminants, as well as other benefits that will be apparent to those skilled in the art from the present disclosure.

In embodiments the ruminant to which a composition of the invention is administered is a member of the genus Bos, such as an ox, cow, or buffalo. In one embodiment the ruminant is a dairy cow.

The present disclosure includes compositions comprising whole cells and/or one or more other immunogens. In embodiments the compositions comprise whole cells selected from whole cells of Escherichia coli (E. coli), Trueperella pyogenes (T pyogenes), Fusobacterium necrophorum (F. necrophorum) and combinations thereof. In embodiments the compositions comprise proteins selected from F. necrophorum leukotoxin (LKT), E. coli type 1 fimbrial adhesin (FimH), T. pyogenes pyolysin (PLO), and combinations thereof. In embodiments the compositions comprise any combinations of the whole cells and the proteins. Thus, the compositions may comprise one, two or three distinct types of bacteria, and/or one, two or three of the proteins. In embodiments, more than one strain of any bacteria type can be included in the veterinary composition. Additional types of bacteria and proteins can also be included.

Any of the proteins described herein can be isolated from bacteria which produce the proteins endogenously and, if desired, purified to any degree of purity. Any of the proteins can also be reproduced recombinantly using conventional techniques, such as by expression using any suitable expression vector and expression system. The amino acid sequences and the polynucleotide sequences encoding the amino acid sequences of each of the proteins described herein are known in the art.

In embodiments, the composition comprises a veterinarily acceptable carrier, excipient or diluent such that the composition is a veterinary composition. Suitable carriers, excipients and diluents are known in the art. In embodiments the veterinary composition functions as a vaccine.

The whole bacterial cells in the veterinary composition can be inactivated using any of a wide variety of methods. Inactivated bacteria are those that have been treated so that they have less pathogenicity relative to bacteria that are not similarly treated. In embodiments the bacteria are inactivated such as by exposure to an organic solvent, one non-limiting example of which is formalin.

The veterinary compositions may also comprise any other agents that would be expected to provide a therapeutic and/or prophylactic benefit to the recipient, such as antibiotics and/or adjuvants. Adjuvants that are suitable for use with veterinary compositions are well known in the art. In one embodiment, the adjuvant is aluminum hydroxide. Non-limiting examples of other adjuvants include liposomes and archaeosomes, calcium salts, oil emulsions, nanoparticles and microparticles, saponins, immune-stimulating complexes, nonionic block copolymers, derivatized polysaccharides, carrier proteins, bacterial products and their derivatives, cytokines, complement derivatives, and others. In certain embodiments, the method can be performed prior to, concurrently, or subsequent to conventional anti-bacterial and anti-inflammatory approaches, including but not limited to antibiotic regimens.

In an embodiment, the present disclosure includes an article of manufacture comprising packaging and at least one sealed container. The sealed container can comprise the veterinary compositions. The veterinary compositions comprise whole cells selected from E. coli, T. pyogenes, F. Necrophorum and combinations thereof. The container can comprise proteins selected from F. necrophorum LKT, E. coli FimH, T. pyogenes PLO, and combinations thereof. In embodiments the container includes any combinations of the whole cells and the proteins. In embodiments, the packaging can have more than one container which separately contains any one or any combination of the cells and/or the proteins. The packaging comprises printed material providing an indication that the veterinary composition is for administration to a ruminant and can include a description of subcutaneous administration, and an indication that the administration is for prophylaxis of metritis in a ruminant, and/or to improve the reproductive function of the ruminant.

The disclosure provides methods for making veterinary compositions and articles of manufacture. The method of making a veterinary composition comprises providing whole cells of E. coli, and/or T. pyogenes, and/or F. necrophorum, and/or LKT, and/or FimH, and/or PLO, and combining one or more of these agents with a veterinarily acceptable carrier, excipient and/or diluent to provide a veterinary composition for use in prophylaxis of metritis and/or for use in improving the reproductive function of a ruminant. To make an article of manufacture, the veterinary compositions are placed in suitable containers and packaged. The package is made to include printed material which provides an indication that the veterinary compositions are for use in subcutaneous administration for the prophylaxis of metritis, and/or for improving the reproductive function of ruminants. The printed material can be part of the packaging material, or it can be a paper insert, or it can be a label affixed to, for example, the container(s).

In another aspect the present disclosure includes a method of stimulating an immune response in a ruminant. The method comprises administering a veterinary composition described herein to a ruminant. The immune response can comprise a humoral and/or cell mediated response. The humoral response can comprise an increase in immunglobulins specific for any antigen expressed by the bacteria, and/or specific for any of the proteins administered in the veterinary composition. In embodiments the stimulated immunoglobulins are IgG. The immune response in certain embodiments provides a prophylactic effect against puerperal metritis. The terms "Prophylaxis" and "prophylactic" as used herein means at least partial inhibition of the formation and/or persistence of symptoms associated with a uterine disease, and in particular with puerperal metritis.

Those skilled in the art will be able to determine, given the benefit of the present disclosure, when and how frequently to administer the compositions and how much of each immunogenic agent to include. In general, factors that will go into this determination include but are not necessarily limited to the type, size, age and overall health of the ruminant. In embodiments, the compositions are administered to the ruminant prior to parturition, but can be administered during pregnancy or any time during the life cycle.

In certain embodiments of the present disclosure subcutaneous administration of a veterinary composition to a ruminant lessens an increase in rectal temperature of the ruminant due to a bacterial infection, relative to the rectal temperature of a ruminant with the bacterial infection but to which the veterinary compositions was not administered.

In an embodiment, administering a veterinary composition described herein to a ruminant improves the reproductive function of the ruminant. An improvement in reproductive function can comprise a reduction in a calving-to-conception interval relative to the calving-to-conception interval in a ruminant to which a veterinary composition has not been administered.

In embodiments the present disclosure includes lowering the incidence of puerperal metritis in a group of animals comprising administering a veterinary composition as described herein subcutaneously to members of a group of animals such that the incidence of puerperal metrtitis in the group of animals is lower than if the composition had not been administered. In certain embodiments the group of animals is dairy cows. The group of animals can be present in, for example, a dairy farm of any scale, ranging from a few dairy cows to a commercial dairy farm which may house thousands of dairy cows.

The following examples are presented to illustrate the present disclosure. They are not intended to limiting in any manner.

EXAMPLE 1

This example shows the relationship between bacterial species-specific virulence factors (VFs) present in the uterus at 3 different stages of lactation (1-3, 8-10, and 34-36 Days In Milk (DIM)) and the incidence of metritis and clinical endometritis in dairy cows. The following VF genes were investigated: plo (pyolysin), cbpA (collagen-binding protein), and fimA (fimbriae expression) which are *Arcanobacterium pyogenes* specific; fimH (a type 1 pilus component), *Escherichia coli* specific; and lktA (leukotoxin), *Fusobacterium necrophorum* specific. Uterine swabs were collected from 111 postpartum dairy cows. PCR was used to detect the presence of plo, cbpA, fimA, fimH, and lktA genes. *A. pyogenes* cbpA was detected in only 5 samples and therefore was not subjected to further analysis. *E. coli* (fimH) was significantly associated with metritis and endometritis when detected at 1-3 DIM; *F. necrophorum* (lktA) was significantly associated with metritis when detected at 1-3 and 8-12 DIM and with endometritis when detected at 34-36 DIM; and *A. pyogenes* (fimA and plo) was associated with metritis (fimA) when detected at 1-3 DIM and endometritis (fimA and plo) when detected at 8-10 and 34-36 DIM.

Farm, Management and Sample Collection.

Uterine swabs were collected from 111 post-partum dairy cows that were housed on a commercial dairy farm located near Ithaca, N.Y. Samples were collected from April 2010 through June 2010. Reproductive management utilized a combination of Presynch, Ovsynch, Resynch, and detection of estrus, with 25 to 30% of cows bred via TAI and the remainder bred after detection of estrus solely by activity monitors (ALPRO; DeLaval, Kansas City, Mo.). Uterine secretion samples were collected from each cow three times during the study period (at 1-3 DIM, at 8-10 DIM, and at 34-36 DIM). Two uterine sample collection methods were used: uterine swab for the first and second sample and uterine lavage for the third sample. At 34-36 DIM the uterus has usually involuted and uterine fluid volume has decreased. Thus, at this point, performing uterine lavage is probably a better way of sampling. Furthermore, uterine lavage was also used at 34-36 DIM for the diagnosis of endometritis. Uterine swabs were collected as follows: cows were restrained and the perineum area was cleansed and disinfected with 70% ethanol. Then, a sterile swab (Har-Vet™ McCullough Double-Guarded Uterine Culture Swab, Spring Valley, Wis.) covered by a sterile pipette (inside a plastic sheath) was introduced to the cranial vagina. The pipette was manipulated through the cervix into the uterus, the sheath was then ruptured, and the swab was exposed to uterine secretion. The swab was pulled inside the pipette and kept in transportation medium at 4° C. until it was processed in the laboratory. Uterine lavage samples were collected. Briefly, cows were restrained and the perineum area was cleansed and disinfected with 70% ethanol. A plastic infusion pipette (inside a plastic sheath) was introduced to the cranial vagina. The sheath was subsequently ruptured, and the clean pipette tip was manipulated through the cervix into the uterus. A total of 40 ml of sterile saline solution was injected into the uterus, agitated gently, and a sample of the fluid aspirated. The volume of recovered fluid ranged from 5 to 15 ml. Samples were kept in ice prior to laboratory processing. This project proposal was reviewed and approved by the Cornell University Institutional Animal Care and Use Committee (#2011-0111).

Case Definition.

Puerperal metritis was clinically defined as an abnormally enlarged uterus and a fetid, watery, red-brown uterine discharge, with signs of systemic illness (decreased milk yield, dullness or other signs of toxemia) at 8-10 days after parturition and diagnosed by one of the veterinarians of the research team. Clinical endometritis of an obtained uterine lavage sample was evaluated at 34-36 DIM by visual inspection. In this way we were able to ensure that visible signs of inflammation (purulent or mucupurulent exudate) emanated from the uterus, rather than from another site. All of the uterine lavage samples were visually scored by one investigator, who assessed the presence of a purulent or mucopurulent secretion in the uterine lavage sample. The score ranged from 0 to 2, with 0 indicating absence of a purulent or mucopurulent secretion in the lavage sample, 1 indicating a bloody but not purulent sample, and 2 the presence of pus in the lavage sample. Cows with a score of 2 were considered as diagnosed with clinical endometritis. Body condition scores were recorded at the time of each uterine lavage using a five-point scale with a quarter-point system. Additionally, farm recorded calving ease score 1-5 (1 and 2 were non-assisted parturitions and 3-5 were assisted partitions with increasing degree of difficulty), stillbirth parturition, and retained placenta incidence were used as risk factors.

agarose gel, stained with 0.5 µg/ml ethidium bromide, and visualized with a Kodak Gel Logic 100 Imaging System (GL 100, Scientific Imaging Systems, Eastman Kodak Co., New Haven, Conn.). Positive results were considered to be amplicons of the expected molecular size.

TABLE 1

PCR primers and reaction conditions used to amplify virulence factor gene sequences.

| Target gene | Primer sequence(5'-3') | Annealing temperature (° C.) | Amplicon Size (bp) |
|---|---|---|---|
| plo | Forward-TCATCAACAATCCACGAAGAG (SEQ ID NO: 1)<br>Reverse-TTGCCTCCAGTTGACGCTTT (SEQ ID NO: 2) | 60 | 150 |
| cbpA | Forward-GCAGGGTTGGTGAAAGAGTTTACT (SEQ ID NO: 3)<br>Reverse-GCTTGATATAACCTTCAGAATTTGCA (SEQ ID NO: 4) | 60 | 124 |
| fimA | Forward-CACTACGCTCACCATTCACAAG (SEQ ID NO: 5)<br>Reverse-GCTGTAATCCGCTTTGTCTGTG (SEQ ID NO: 6) | 57 | 605 |
| fimH | Forward-TGCAGAACGGATAAGCCGTGG (SEQ ID NO: 7)<br>Reverse-GCAGTCACCTGCCCTCCGGTA (SEQ ID NO: 8) | 63 | 508 |
| lktA | Forward-AATCGGAGTAGTAGGTTCTG (SEQ ID NO: 9)<br>Reverse-TTTGGTAACTGCCACTGC (SEQ ID NO: 10) | 60 | 401 |

DNA Extraction, PCR, Gel Electrophoresis and Sequencing.

Swab samples were immersed in 1 ml of phosphate-buffered saline (PBS) into a 15-ml Falcon tube and vortexed to disperse any mucus, bacteria, cells, or transport culture medium. Isolation of total DNA was performed from 400 µl of the suspension by using a QIAmp DNA minikit (Qiagen, Santa Clara, Calif.) according to the manufacturer's instructions for DNA purification from blood and body fluids. Some convenient modifications, such as addition of 400 µg of lysozyme and incubation for 12 h at 56° C., were included to maximize bacterial DNA extraction. Total DNA was eluted in 100 µl of sterile DNase/RNase-free water (Promega, Madison, Wis.). DNA concentration and purity were evaluated by optical density using the Nanodrop ND-1000 spectrophotometer (Nanodrop Technologies, Rockland, Del.).

PCR was used for the amplification of specific VFs genes' parts. Among the VF genes that contribute to the pathogenic potential of *A. pyogenes*, three were amplified: plo, cbpA and fimA. To categorize *E. coli*, the fimH gene was chosen. The leukotoxin gene (lktA), which appears to be unique for *F. necrophorum*, was used as that bacterium's VF. Details regarding the primer sequences, annealing temperatures, and size of amplicons can be found in Table 1. Presence of known and putative *A. pyogenes, E. coli* and *F. necrophorum* VF genes was assessed independently. Thermal cycling parameters were adjusted according to the target sequence, as described in Table 1. All reactions were performed in a 25-µl volume using 24 µl of 1× Green GoTaq Master Mix (made from 2× Green GoTaq Master Mix consisting of Green GoTagReaction Buffer, 400 µM dATP, 400 µM dGTP, 400 µM dCTP, 400 µM dTTP, and 3 mM MgCl$_2$; Promega Corp., Madison, Wis.) and primers, and 1 µl of DNA extract. All thermal cycling protocols were performed in a 2720 Thermal Cycler (Applied Biosystems, Foster City, Calif.). Negative controls consisting of the PCR mixture without DNA were included in all PCR runs. Amplification products were separated by electrophoresis through a 1.2% (wt/vol)

To confirm the origin of the PCR products, a random sample of 5 PCR positive samples from each of the genes fimH, plo, fimA, and lkta was purified and submitted to sequencing. The sequences obtained were compared to sequences in GenBank using the BLAST algorithm. All sequences matched their respective genes with a sequence identity>98%.

Statistical Analysis.

Cows were dichotomized several times into VF positive (1) or VF negative (0). To evaluate the relationship between VF-gene presence and the odds of metritis and clinical endometritis, two multivariable logistic regression models were fitted to the data; dependent variables were metritis (yes-no) and clinical endometritis (yes-no). The independent variables offered to the models were: assisted parturition (calving ease score≥3), retained placenta, parity group (1, 2, ≥3), body condition score, and the VFs fimH, plo, fimA, and lktA on DIM 1-3, 8-10, and 34-36. All possible two-way interaction terms were added to the model. Variables were manually and stepwise removed from the models in descending order of P-value (backward elimination). Statistical significance was considered when a P<0.05 was observed. Another set of multivariable logistic regressions was performed to evaluate the association between risk factors (assisted parturition, retained placenta, parity, body condition score), and the preceding VFs that were significantly associated with uterine disease.

Kaplan-Meier survival analysis was performed to evaluate association of VF genes (plo, cbpA, fimA, fimH, and lktA) with reproductive performance using Medcalc version 10.4.0.0 (Mariakerke, Belgium); the Logrank test was used to compute P-values. The time series variable for this model was the calving-to-conception interval or days from calving until the end of the follow-up period; the minimum follow up period was 150 and the maximum was 250. Statistical significance was considered when P<0.05 was observed.

The following results were obtained using the materials and methods described above.

Descriptive Statistics.

A total of 111 Holstein cows were used in this study, of which 56 (50.4%) were primiparous, 34 (30.6%) were second parity, and 21 (18.9%) were third parity or greater. The *A. pyogenes* VF cbpA was not identified at first sampling (1-3 DIM), and 2 and 3 cows were identified at 8-10, and 34-36 DIM, respectively. Because of its low prevalence VF cbpA was excluded from all disease association analyses. The *A. pyogenes* VFs fimA and plo were prevalent at all 3 different samplings (1-3, 8-10, and 34-36 DIM) and the highest prevalence was observed at 8-10 DIM (FIG. 1). The most prevalent VF was the *F. necrophorum* VF lktA, which encodes an exotoxin (leukotoxin). The *E. coli* VF fimH was also detected at all 3 sampling periods, being most prevalent at 8-10 DIM (FIG. 1). The total incidence of metritis in this study population was 40.5%, and the prevalence of clinical endometritis diagnosed at 34-36 DIM was 19.8%.

Association of Bacterial Species-Specific Virulence Factors and the Prevalence of Metritis.

Two variables were found to significantly ($P<0.05$) affect prevalence of metritis: *E. coli* fimH presence at 1-3 DIM and *F. necrophorum* lktA diagnosed at 8-10 DIM (Table 2). Cows contaminated with fimH positive *E. coli* had a 4.7 times higher odds of developing metritis compared to fimH negative cows (P-value<0.001). *F. necrophorum* VF lktA was the only VF detected at 8-10 DIM that was significantly associated with metritis; prevalence of metritis was 54.1% for lktA positive cows and 24% for lktA negative cows (Table 2).

TABLE 2

Risk factors with a significant effect on the odds of metritis diagnosed at 8-10 DIM.

| Risk factors | Number of cows | Metritis % | Odds ratio | P-value |
|---|---|---|---|---|
| *E. coli* fimH 1-3 postpartum | | | | |
| POSITIVE | 21 | 76.2% | 4.7 | <0.01 |
| NEGATIVE | 90 | 32.2% | Ref. | |
| *F. necrophorum* lktA 8-10 postpartum | | | | |
| POSITIVE | 61 | 54.1% | 2.6 | 0.03 |
| NEGATIVE | 50 | 24.0% | Ref. | |

Association of Bacterial Species-Specific Virulence Factors and the Prevalence of Clinical Endometritis.

Three variables were found to significantly ($P<0.05$) affect prevalence of metritis: *E. coli* fimH presence at 1-3 DIM and *A. pyogenes* fimA diagnosed at 8-10 and 34-36 DIM (Table 3). *E. coli* VF fimH was associated with a significantly increased prevalence of endometritis only when detected in the first sample collection (DIM 1-3); the prevalence of endometritis was 38.1% and 15.6% for fimH positive and negative cows, respectively (P-value<0.01). *Arcanobacterium pyogenes* fimA was highly associated with clinical endometritis when detected at 8-10 and 34-36 days post-partum; cows that were fimA positive at 34-36 DIM were at 8.8 times higher odds of clinical endometritis compared to negative cows.

TABLE 3

Risk factors with a significant effect on the odds of clinical endometritis diagnosed at 34-36 DIM

| Risk factors | Number of cows | Endometritis % | Odds ratio | P-value |
|---|---|---|---|---|
| *E. coli* fimH1-3 postpartum | | | | |
| POSITIVE | 21 | 38.1% | 5.4 | 0.01 |
| NEGATIVE | 90 | 15.6% | Ref. | |
| *A. pyogenes* fimA 8-10 postpartum | | | | |
| POSITIVE | 39 | 33.3% | 5.6 | <0.01 |
| NEGATIVE | 72 | 12.5% | Ref. | |
| *A. pyogenes* fimA 34-36 postpartum | | | | |
| POSITIVE | 13 | 61.4% | 8.8 | <0.01 |
| NEGATIVE | 98 | 14.3% | Ref. | |

Risk Factors for fimH at 1-3 DIM, fimA at 8-10 and 34-36 DIM, and lktA at 8-10 DIM.

Results regarding risk factors with a significant effect on prevalence of specific VFs (fimH at 1-3 DIM, fimA at 8-10 and 34-36 DIM, and lktA at 8-10 DIM) are presented in Table 4. Cows with a retained placenta were at a 44.8 times higher odds of being contaminated with fimH positive *E. coli* compared to cows without a retained placenta and this was the stronger effect observed.

TABLE 4

Outcomes of 4 different multivariable logistic regression models that evaluated the association of several risk factors with the odds of prevalence of the virulence factors fimH (1-3 DIM), fimA (8-10 DIM), fimA (34-36 DIM), and lktA (8-10 DIM).

| Risk factors | n | % | Odds ratio | P-value |
|---|---|---|---|---|
| fimH positive 1-3 DIM | | | | |
| Retained placenta | | | | |
| Yes | 10 | 90.0% | 44.8 | <0.01 |
| NO | 101 | 11.9% | Ref. | |
| *F. necrophorum* lktA 1-3 postpartum | | | | |
| POSITIVE | 27 | 44.4% | 4.2 | 0.02 |
| NEGATIVE | 84 | 10.7% | Ref. | |
| fimA positive 8-10 DIM | | | | |
| *F. necrophorum* lktA 1-3 postpartum | | | | |
| POSITIVE | 27 | 11.1% | 0.12 | <0.01 |
| NEGATIVE | 84 | 42.9% | Ref. | |
| *F. necrophorum* lktA 8-10 postpartum | | | | |
| POSITIVE | 61 | 42.6% | 2.9 | 0.01 |
| NEGATIVE | 50 | 26.0% | Ref. | |
| fimA positive 34-36 DIM | | | | |
| Ease of parturition | | | | |
| Assisted | 10 | 40.0 | 7.2 | 0.03 |
| Non-assisted | 101 | 8.9 | Ref. | |
| *F. necrophorum* lktA 1-3 postpartum | | | | |
| POSITIVE | 27 | 29.6% | 5.8 | 0.02 |
| NEGATIVE | 84 | 5.9% | Ref. | |
| *F. necrophorum* | | | | |

TABLE 4-continued

Outcomes of 4 different multivariable logistic regression models that evaluated the association of several risk factors with the odds of prevalence of the virulence factors fimH (1-3 DIM), fimA (8-10 DIM), fimA (34-36 DIM), and lktA (8-10 DIM).

| Risk factors | n | % | Odds ratio | P-value |
|---|---|---|---|---|
| lktA34-36 postpartum | | | | |
| POSITIVE | 14 | 57.1% | 18.8 | <0.01 |
| NEGATIVE | 97 | 5.1% | Ref. | |
| lktA positive 8-10 DIM | | | | |
| Ease of parturition | | | | |
| Assisted | 10 | 90.0% | 12.6 | 0.02 |
| Non-assisted | 101 | 51.5% | Ref. | |
| E. coli fimH 1-3 postpartum | | | | |
| POSITIVE | 21 | 90.5% | 16.2 | <0.01 |
| NEGATIVE | 90 | 46.7% | Ref | |

Association of Bacterial Species-Specific Virulence Factors with Reproductive Performance.

Figure 2:
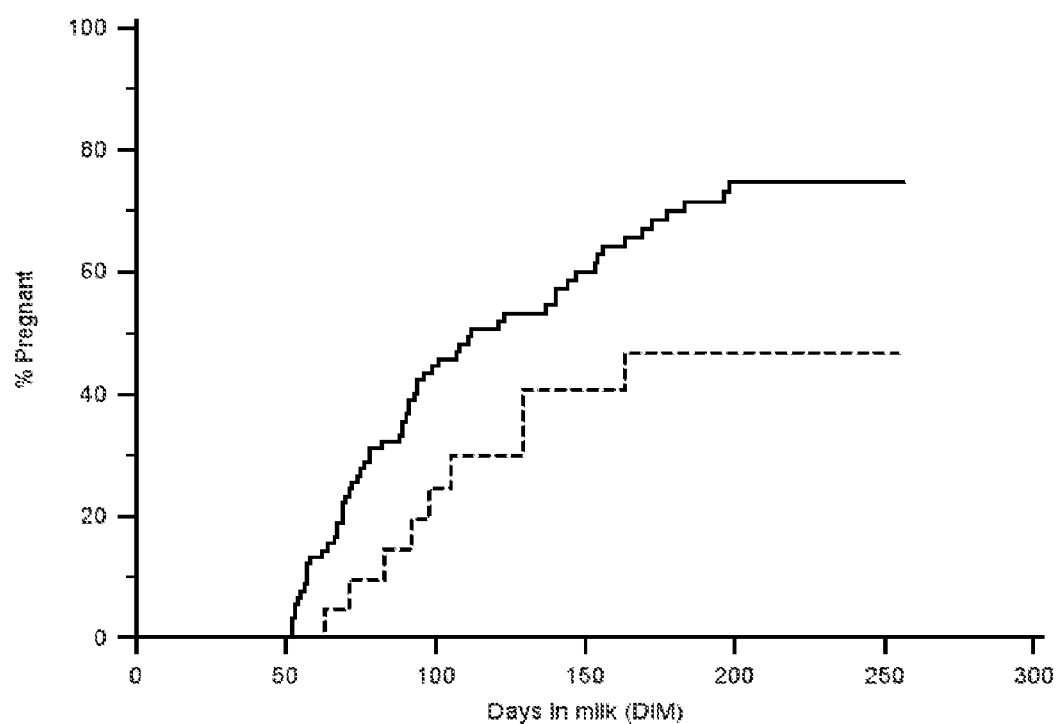
FIG. 2 shows an example of an effect of fimH detection at 1-3 days in milk (DIM) on reproductive performance. The solid black line represents fimH negative cows and the interrupted line fimH positive cows. fimH positive cows were 2.1 times less likely to be confirmed pregnant than fimH negative cows (P<0.001).

The only VF significantly associated with reproductive performance was fimH at 1-3 DIM; cows that were fimH positive at the first sampling were 2.1 times less likely to be confirmed pregnant when compared to fimH negative cows (P<0.01, FIG. 2). As will be apparent from the foregoing, in this example, presence of fimH-carrying E. coli at 1-3 DIM was strongly associated with metritis and clinical endometritis. However, E. coli was not associated with uterine diseases when detected at later stages of lactation (8-10 and 34-36 DIM), suggesting that E. coli is likely among the first bacteria to colonize the intrauterine environment, potentially inducing changes that will favor future colonization by strict (F. necrophorum) and facultative (A. pyogenes) anaerobic bacteria which will ultimately cause clinical signs of uterine disease. Intrauterine pathogenic E. coli (IUPEC) possesses an arsenal of VFs (fimH, hlyA, cdt, kpsMII, ibeA, and astA) associated with extraintestinal pathogenic E. coli (ExPEC). Of the six VFs associated with metritis and endometritis, fimH was the most significant because of its high prevalence and strong association with uterine diseases and reproductive failure.

FimH is an adhesin (from type-1 pilus) that belongs to a family of proteins involved in bacterial adherence to various targets, including host mammalian cells. Results from one previous study showed that clonal E. coli isolated from metritic cows were more adherent to and invasive into endometrial epithelial and stromal cells than were clonal bacteria isolated from clinically unaffected animals. Another study also concluded that the bacteria lacked pathogenicity genes typically associated with virulence in E. coli—they evaluated 17 VF genes and none were found to be associated with uterine disease.

In the this example, FimH positive cows at 1-3 DIM were 16.2 times more likely to develop F. necrophorum intrauterine contamination at 8-10 DIM. These findings support the notion that establishment and persistence of uterine infection by F. necrophorum and other gram-negative anaerobic bacteria are influenced by the presence of a suitable intrauterine environment established by a preceding E. coli infection. Furthermore, in the present study, the presence of fimH-carrying E. coli at 8-10 or 34-36 DIM was not associated with metritis, clinical endometritis or reproductive failure. In fact, fimH positive cows at 8-10 DIM had a numerically lower incidence of metritis (32.1%) when compared to fimH negative cows (43.4%). This fact highlights the multifactorial etiology of postpartum uterine diseases and the hypothesis that the intrauterine microbial population shifts as cows advance into their lactation. Over 90% of the fimH positive cows at 1-3 DIM were contaminated with F. necrophorum one week later and the presence of F. necrophorum was an important risk factor for the appearance of A. pyogenes.

Samples collected at 8-10 DIM presented the highest bacterial prevalence compared to the other two stages of lactation—at least one VF was present in 71% of cows. Interestingly, A. pyogenes and F. necrophorum were found to predominate in the samples from the second collection period. At 8-10 DIM the VF lktA was the only VF strongly associated with metritis: the prevalence of metritis was 54.1% for F. necrophorum positive cows and 24% for the negative cows.

In this example, uterine contamination by F. necrophorum and A. pyogenes was found to be highest in the second and third sampling periods, respectively, in cows that needed assistance during parturition. Both A. pyogenes and F. necrophorum were strongly associated with clinical endometritis when detected at the third sampling period (DIM 34-36) in the study in this example.

In this example, retained placenta increased the odds of intrauterine contamination by fimH positive E. coli by 44.8 times. Additionally, cows that had assisted parturition were at higher risk of F. necrophorum and A. pyogenes contamination. Hence, uterine disease is influenced by parturition events and environmental bacterial contamination plays an important role.

This example provides evidence that the bacterial etiology of postpartum uterine diseases is dynamic and multifactorial, with a significant contribution from at least three different bacteria: Escherichia coli, Fusobacterium necrophorum, and Arcanobacterium pyogenes.

Finally, cows that were fimH positive on the first sampling (DIM 1-3) were 2.1 times less likely to become pregnant compared to fimH negative cows; fimH was the only VF gene significantly associated with reduced reproductive performance.

The E. coli specific fimH and the F. necrophorum specific lktA VF genes were significantly associated with a higher prevalence of metritis when detected at 1-3 and 8-10 DIM, respectively. The E. coli specific fimH and the A. pyogenes specific fimA VF genes were significantly associated with clinical endometritis when detected at 1-3 days (fimH) and at 8-10 and 34-36 (fimA) DIM.

EXAMPLE 2

In this example, the efficacy of five vaccine formulations containing different combinations of proteins (FimH; leukotoxin, LKT; and pyolysin, PLO) and/or inactivated whole cells (Escherichia coli, Fusobacterium necrophorum, and Trueperella pyogenes) for prophylaxis of postpartum uterine diseases was studied. Our initial expectation was that prepartum immunization against relevant antigens for postpartum uterine diseases would prevent the occurrence of puerperal metritis and endometritis.

As described further below, inactivated whole cells were produced using two genetically distinct strains of each bacterial species (E. coli, F. necrophorum, and T. pyogenes). FimH and PLO subunits were produced using recombinant protein expression, and LKT was recovered from culturing a wild F. necrophorum strain. Three subcutaneous vaccines were formulated: Vaccine 1 was composed of inactivated bacterial whole cells and proteins; Vaccine 2 was composed of proteins only; and Vaccine 3 was composed of inactivated bacterial whole cells only. Two intravaginal vaccines were formulated: Vaccine 4 was composed of inactivated bacterial whole cells and proteins; and Vaccine 5 was composed of PLO and LKT. To evaluate vaccine efficacy, a randomized clinical trial was conducted at a commercial dairy farm; 371 spring heifers were allocated randomly into one of six different treatments groups: control, Vaccine 1, Vaccine 2, Vaccine 3, Vaccine 4 and Vaccine 5. Late pregnant heifers assigned to one of the vaccine groups were each vaccinated twice: at 230 days and 260 days of pregnancy. When the vaccines were evaluated and grouped as subcutaneous and intravaginal, the subcutaneous ones were found to significantly reduce the incidence of puerperal metritis. Additionally, subcutaneous vaccination significantly reduced rectal temperature at 6±1 days in milk. Reproductive performance was improved for cows that received subcutaneous vaccines. In general, vaccination induced a significant increase in serum IgG titers against all antigens, with subcutaneous vaccination again being more effective. In conclusion, subcutaneous vaccination with inactivated bacterial components and/or protein subunits of *E. coli, F. necrophorum* and *T. pyogenes* can prevent successfully puerperal metritis during the first lactation of dairy cows, leading to improved reproductive performance.

Materials and Methods. Inactivated bacterial components. *E. coli* strains 4612-2 and 12714-2 were used for this Example. Strains were grown aerobically on Luria-Bertani (LB) broth (Sigma-Aldrich) at 37° C. They were inoculated with 1% of an overnight culture and grown in 800 ml of medium, with agitation (150 rpm). For strain 12714-2, cells were harvested at 4 h, with an $OD_{600}$ of 0.432 and $1.0 \times 10^9$ CFU/ml; for strain 4612-2, cells were harvested at 3.5 h, $OD_{600}$ of 0.473 and $1.2 \times 10^9$ CFU/ml. The cultures were inactivated with 0.1% formalin for 12 h, and the cells were concentrated 4-fold (final volume of 200 ml), so 0.25 ml of each strain would be present in the final vaccine formulation, with approximately $10^9$ CFU per dose.

*Trueperella pyogenes* strains 10481-8 and 6375-1 were isolated from the uterine lumen of dairy cows. Strains were grown on VersaTREK REDOX 1 (Trek Diagnostic Systems, OH) in 7% $CO_2$ at 37° C. Cells were harvested at 48 h, with $1.3 \times 10^8$ and $0.5 \times 10^8$ CFU/ml for strains 10481-8 and 6375-1, respectively. The cultures were inactivated with 0.1% formalin for 12 h, and 1 ml of each strain was added to the final vaccine formulation, with approximately $10^8$ CFU per dose.

*Fusobacterium necrophorum* strains 5663 and 513 were isolated from the uterine lumen of dairy cows. Strains were grown on VersaTREK REDOX 2 (Trek Diagnostic Systems, OH) anaerobically at 37° C. All cultures were inactivated with 0.1% formalin for 12 h before the cells were concentrated. Cells were harvested at 12 h, with $1.6 \times 10^{12}$ and $1.8 \times 10^{12}$ CFU/ml for strains 513 and 5663, respectively. The cultures were inactivated with 0.1% formalin for 12 h, and 0.01 ml of each strain was added to the final vaccine formulation, with approximately $10^{10}$ CFU per dose.

Recombinant protein expression and purification. Bacterial strain growth and induction conditions. *E. coli* TOP10 (Invitrogen, NY) was grown either on LB agar or in LB broth (Sigma-Aldrich, MO) at 37° C. Ampicillin (50 µg/ml) was added as appropriate. *T. pyogenes* 49698 (American Type Culture Collection, VA) was grown on brain heart infusion (BHI) agar or in BHI broth (BD BBL, MD) supplemented with 5% defibrinated horse blood at 37° C. and 7% $CO_2$.

For the preparation of His-tagged proteins (His-PLO or $FimH_{1-156}$-His), appropriate *E. coli* cultures were grown at 37° C. with agitation (200 rpm) to an optical density at 600 nm of ~0.6. At this point, isopropyl 1-thio-β-D-galactopyranoside (IPTG; Sigma) was added to the cultures to 1 mM, which were further incubated with agitation for at least 3 h.

DNA Manipulation and Constructs.

Standard procedures for *E. coli* transformation and plasmid extraction, DNA restriction, ligation, and agarose gel electrophoresis were performed. Primers were synthesized by IDT, and PCRs were performed in a GeneAmp PCR System 9700 (Applied Biosystems, CA). To confirm that no mutations were introduced by PCR, all DNA constructs were sequenced using an automated DNA sequencer (Cornell Biotechnology Resource Center, NY) and analyzed using LaserGene software (DNASTAR, WI).

Cloning and Purification of Recombinant His-PLO.

The PLO gene, lacking the coding region for the predicted signal sequence, was amplified from *A. pyogenes* ATCC49698 genomic DNA by PCR with a 5' primer containing an XhoI site (5'-ACAGCATC CTCGAGTGCCGGATTGGGAAAC-3' (SEQ ID NO:11)) and a 3' primer containing an EcoRI site (5'-TG GAATTCCCTAGGATTTGACATTGT-3' (SEQ ID NO:12)). The 50-µl reaction contained 1×Pfx amplification buffer (Invitrogen) with 1 mM $MgSO_4$ (Invitrogen, NY), 0.3 mM of each dNTP, 0.3 µM of each primer, 1 U of Platinum Pfx DNA polymerase (Invitrogen, NY), and approximately 50 ng of template DNA. The cycling parameters for amplification were: initial denaturation for 5 mM at 94° C., followed by 30 cycles of denaturation (94° C. for 1 min), annealing (58° C. for 1 min), extension (72° C. for 3 min), and a final extension at 72° C. for 7 min. The 1.5-kb amplicon was digested with XhoI-EcoRI and cloned into XhoI-EcoRI-digested pTrcHisB (Invitrogen, NY).

After 3 h of induction, the cells were harvested by centrifugation at 10,000×g for 10 min and the pellet was resuspended in 1× Extraction/Wash Buffer (50 mM sodium phosphate, 300 mM NaCl) (pH 7.0). Lysozyme was added to a final concentration of 0.75 mg/ml and the mixture was incubated at 4° C. with shaking for 30 min. The cells were disrupted by two passages through a French pressure cell (Amicon) at 20,000 psi (138 Mpa), and the insoluble material was removed by centrifugation at 12,000×g for 30 min. His-PLO was purified from the soluble fraction with TALON metal affinity resin (Clontech, CA) according to the manufacturer's instructions. Isolated pure protein fraction was concentrated using a fiber concentration/desalting system using a filter with a molecular weight exclusion of 10 kDa (Amicon ultra 100K, Millipore, Mass.) and subjected to SDS-PAGE (15%) using the Mini-PROTEAN Tetra Cell electrophoresis system (Bio-Rad, CA), following standard protocols. Protein concentration was determined by the Bradford method.

A total of 30 liters of culture was grown to produce a total of 321.24 mg of His-PLO. The final volume of His-PLO was 41 ml and the final concentration was 7.83 mg/ml.

Cloning and Purification of Recombinant $FimH_{1-156}$-his.

The portion of the FimH gene encoding the signal peptide and the first 156 amino acids (the mannose-binding lectin domain, LD) of the mature protein was amplified from plasmid pET-22b(+)-F3-LD, provided by Dr. Evgeni Sokurenko, University of Washington, Wash. The 5' primer used contained a BamHI site (5'-CGC GGATCCATGAAACGTGTTATTACCCTG-3' (SEQ ID NO:13)) and the 3' primer contained a HindIII site (5'-CCC AAGCTTCTAGTGATGGTGATGGTGATGGCCGCCAG TAGGCACCAC-3' (SEQ ID NO:14)) and a six-histidine tag following the authentic sequence of the protein. The PCR components were as described for PLO gene amplification. The cycling parameters for amplification were: initial denaturation for 5 min at 94° C., followed by 25 cycles of denaturation (94° C. for 1 min), annealing (61° C. for 1 min), extension (72° C. for 3 min), and a final extension at 72° C. for 7 min. The amplicon, approximately 0.6 kb, was digested with BamHI-HindIII and cloned into BamHI-HindIII-digested pTrcHisA (Invitrogen). After 5 h of induction, $FimH_{1-156}$-His purification was performed as described for PLO.

A total of 92 liters of culture was grown to produce 216.34 mg of $FimH_{1-156}$-His. The final volume of $FimH_{1-156}$-His was 172.5 ml and the concentration was 1.25 mg/ml.

Culture Concentrated Supernatant and Affinity Purification of Leukotoxin.

*F. necrophorum* strain 6586 was grown in VersaTREK REDOX 2 for 12 h anaerobically at 37° C. The culture supernatant was concentrated at 4° C. in a hollow fiber concentration/desalting system using a filter with a molecular weight exclusion of 100 kDa (Amicon ultra 100K, Millipore, Mass.). Affinity purification of LKT was performed to evaluate the concentration of LKT in the *F. necrophorum* 6586 culture concentrated supernatant. Briefly, purified mAb F7B10 (3.5 mg) was coupled to 5 ml of Affi-Gel 10 affinity support (Bio-Rad, CA) and packed in a 1×20 cm column. The *F. necrophorum* 6586 culture concentrated supernatant was applied to the column, and non-binding materials were removed by passing 15 mL of 0.5 M NaCl in PBS through the column Purified LKT was eluted with 0.2 M glycine-HCl (pH 3.0), immediately neutralized with NaOH, and washed and concentrated using an Amicon ultra 10K. Purity of the toxin was determined by SDS-PAGE.

A total of 10 L of *F. necrophorum* 6586 was grown to produce 220 mL of concentrated supernatant containing 0.186 mg/ml of LKT. The presence and concentration of LKT in the concentrated supernatant was determined by affinity purification.

Vaccine formulation. Five different vaccine formulations were made: three subcutaneous vaccines (Vaccines 1-3) and two intravaginal vaccines (Vaccine 4-5). Vaccine 1 was composed of inactivated bacterial whole cells (*E. coli, T. pyogenes* and *F. necrophorum*) and proteins (FimH, PLO and LKT); Vaccine 2 was composed only of proteins (FimH, PLO and LKT); and Vaccine 3 was composed only of inactivated bacterial whole cells (*E. coli, T. pyogenes* and *F. necrophorum*). Vaccine 4 was composed of inactivated bacterial whole cells (*E. coli, T. pyogenes* and *F. necrophorum*) and proteins (FimH, PLO and LKT), and Vaccine 5 was composed only of proteins (PLO and LKT). The adjuvant for the subcutaneous vaccines was aluminum hydroxide (Rehydragel HPA, General Chemical, NJ). The adjuvant volume used in the subcutaneous vaccines was 25% of the final vaccine volume. Aluminum hydroxide was added to each component separately, and it was gently stirred overnight. The adjuvant for the intravaginal vaccines was 20 µg/dose of Cholera toxin (List Biological Laboratories, Inc., CA).

All vaccine components were tested for sterility before the final vaccine was assembled and bottled. Sterility was evaluated by culturing 100 µl of vaccine component aerobically in LB broth, aerobically in 7% $CO_2$ on VersaTREK REDOX 1 and anaerobically on VersaTREK REDOX 2 at 37° C. for 48 h. Components were considered contaminated if there was bacterial growth in any of the three culture media by the end of the incubation period.

Assessment of endotoxin levels was performed using the LAL Endpoint Assay (Hycult Biotech, The Netherlands) following the manufacturer's instructions. All vaccine formulations had endotoxin levels below $10^5$ EU/ml.

Farm and management. The field trial was conducted in a commercial dairy farm located near Ithaca, N.Y. Cows were enrolled from May 24, 2012 to Aug. 16, 2012; the follow-up period continued until Apr. 30, 2013. This farm was selected because of its long working relationship with the Ambulatory and Production Medicine Clinic at Cornell University. The research protocol was reviewed and approved by the Institutional Animal Care and Use Committee of Cornell University (Protocol number: 2011-0111). The farm milked 3,300 Holstein cows 3 times daily in a double 52-stall parallel milking parlor. The cows were housed in freestall barns with concrete stalls covered with mattresses and bedded with manure solids. All cows were offered a total mixed ration (TMR) consisting of approximately 55% forage (corn silage, haylage, and wheat straw) and 45% concentrate (corn meal, soybean meal, canola, cottonseed, and citrus pulp) on a dry matter basis of the diet. The diet was formulated to meet or exceed the NRC nutrient requirements for lactating Holstein cows weighing 650 kg and producing 45 kg of 3.5% fat corrected milk. The reproductive management utilized a combination of Presynch, Ovsynch, Resynch, and detection of estrus, with 25% to 30% of cows bred via timed artificial insemination and the remainder bred after detection of estrus solely by activity monitors (AL-PRO; DeLaval, Kansas City, Mo.).

Treatment groups and Case definition. Late pregnant heifers were enrolled on a weekly basis; inclusion criteria for enrollment were: 230±3 days of pregnancy, 629 to 734 days of age and body condition score (BCS) greater than 2.5. Heifers that were visually lame were not included in the study. A total randomized field trial study design was used; heifers were randomly allocated into one of six different treatment groups using the random number function of Excel (Microsoft, Redmond, Mass.). A total of 371 pregnant heifers were enrolled in the study; 105, 54, 54, 53, 53 and 53 heifers were randomly allocated to the control, Vaccine 1, Vaccine 2, Vaccine 3, Vaccine 4 and Vaccine 5 groups, respectively. Heifers assigned to the vaccine groups received two doses of vaccine: at 230±3 days of pregnancy and 260±3 days of pregnancy.

Body condition scores were determined for all study cows at 230±3 days of gestation, 260±3 days of gestation, 2±1 days in milk (DIM), 6±1 DIM and at 35±3 DIM by a single investigator blinded to treatment group using a five-point scale with a quarter-point system. To obtain serum samples, blood was collected from a coccygeal vein/artery using a Vacutainer tube without anticoagulant and a 20 gauge×2.54 cm Vacutainer needle (Becton, Dickinson and Company, Franklin Lakes, N.J.). All blood samples were transported to the laboratory on ice and spun in a centrifuge at 2,000×g for 15 min at 4° C.; serum was harvested and frozen at −80° C. Serum samples were collected at 230±3 days of gestation, 260±3 days of gestation, 1±2 DIM, 6±1 DIM and 35±3 DIM.

Cervical swabs were collected at 2±1 DIM and 6±1 DIM; cows were restrained and the perineum area was cleansed and disinfected with 70% ethanol solution. The swab was manipulated inside the cervix and exposed to uterine secretion. The swabs were kept inside a sterile vial at 4° C. until processed in the laboratory. Swabs collected at 2±1 DIM were cultured aerobically on Chromagar (Difco) at 37° C. and *E. coli* colonies were distinguished by a blue color;

swabs collected at 6±1 DIM were cultured anaerobically on LKV agar (Anaerobe Systems) and *F. necrophorum* colonies were distinguished by morphology.

Retained placenta, puerperal metritis, ketosis, and clinical mastitis were diagnosed and treated by trained farm personnel who followed a specific diagnostic protocol designed by veterinarians from the Ambulatory and Production Medicine Clinic, Cornell University. Farm personnel were blinded to the treatments.

After parturition, cows were kept in the same pen until around 20 DIM. This pen was monitored intensively by farm employees, and cows were submitted to a complete physical exam if they were showing signs of dullness and depression; cows with fetid, watery, red-brown uterine discharge accompanied with fever were diagnosed with puerperal metritis and treated by farm employees. Retained placenta was defined as a condition where cows failed to release their fetal membranes within 24 h of calving. Puerperal metritis diagnosis by the research team was performed at 6±1 DIM. Puerperal metritis was defined as the presence of fetid, watery, red-brown uterine discharge and rectal temperature greater than 39.5° C. Information regarding puerperal metritis diagnosis was not exchanged between farm personnel and the research team. Data regarding health traits and reproduction were extracted from the farm's DairyComp 305® database (Valley Agricultural Software, Tulare, Calif.).

Clinical endometritis diagnosis was evaluated at 35±3 DIM by visual inspection of a uterine lavage sample for the presence of purulent secretion. To obtain uterine lavage samples, the cows were restrained, the perineum area was cleansed and disinfected with 70% ethanol, and a plastic infusion pipette was introduced into the cranial vagina and manipulated through the cervix into the uterus. A total of 20 ml of sterile saline solution was infused into the uterus and agitated gently, and a sample of the fluid was aspirated. The volume of recovered fluid ranged from 5 to 15 ml. All samples were visually scored by one investigator, who assessed the presence of a purulent or mucopurulent secretion in the uterine lavage sample. The score ranged from 0 to 2, with 0 indicating absence of a purulent or mucopurulent secretion, 1 indicating a bloody but not purulent sample, and 2 indicating the presence of pus in the lavage sample. Cows with a score of 2 were considered as diagnosed with clinical endometritis. Samples were kept on ice until they were cultured on Mueller-Hinton agar plates (BBL™) supplemented with 5% defibrinated sheep blood for 48 h aerobically in 5% $CO_2$ at 38° C. Typical *T. pyogenes* colonies were distinguished by colony morphology, post-incubation hemolysis, and characteristic appearance on Gram's stain.

Enzyme-linked immunosorbant assays (ELISAs). Portions of the antigens produced for preparation of vaccines were used in ELISAs. *E. coli* strains were pooled together as a single antigen. The same was done for *F. necrophorum* and *T. pyogenes* strains.

Bovine serum samples were thawed and mixed before analysis. The selected ELISA protocols were as follows. ELISA micro-titer plates (Greiner Bio-One, Germany) were coated with PBS (Phosphate-Buffered Saline 10×, pH 7.4, Ambion®) containing either 0.295 µg/ml of $FimH_{1-156}$-His, 0.036 µg/ml of His-PLO, 0.186 µg/ml of LKT, $10^7$ cells/ml of *E. coli*, $10^{10}$ cells/ml of *F. necrophorum*, and $10^7$ cells/ml of *T. pyogenes* for anti-FimH, anti-LKT, anti-PLO, anti-*E. coli*, anti-*F. necrophorum*, and anti-*T. pyogenes* IgG assays, respectively. Binding of antigen to microtiter wells was carried out overnight at 4° C., non-specific binding sites were blocked with PBS containing 1% casein (Thermo Scientific, Rockford, Ill.). Dilutions of bovine serum samples were then added to the ELISA plates; serum samples were diluted in proportions of 1:1000, 1:5000, 1:5000, 1:150, 1:500, and 1:150 for anti-FimH, anti-LKT, anti-PLO, anti-*E. coli*, anti-*F. necrophorum*, and anti-*T. pyogenes* IgG assays, respectively. The optimal antigen and antibody concentrations were determined by performing the quantitative ELISA protocol with varying concentrations. The serotype-specific antibody bound to the ELISA plate was detected with anti-bovine IgG antibody conjugated with horseradish peroxidase, diluted according to the manufacturer's instructions (Sigma Aldrich, St. Louis, Mo.), followed by addition of the substrate, 3,3',5,5'-tetramethylbenzidine—TMB (Sigma Aldrich, St. Louis, Mo.). The optical density of each well was measured after 20 min at 650 nm using an ELISA plate reader (Synergy HTmicroplate reader BioTek Instruments, VT). The amount of color produced was proportional to the amount of primary antibody bound to the proteins on the bottom of the wells. Between each step of the assay, the microtiter wells were aspirated and rinsed 3 times with washing solution (1× Phosphate Buffered Saline Tween-20).

Statistical analyses. Descriptive statistics analysis was undertaken in SAS using the FREQ procedure (SAS Institute INC., Cary, N.C.). To assess the effect of vaccination on the odds of RDPMET, FDPMET, endometritis, *E. coli*, *F. necrophorum*, and *T. pyogenes* culture outcomes, logistic regression models were fitted in SAS using the Logistic procedure. The effect of subcutaneous and intravaginal vaccines on reproduction was analyzed by Cox's proportional hazard using the proportional hazard regression procedure in SAS. To assess the effect of vaccination on rectal temperature at 6±1 DIM, mixed general linear models were fitted to the data using JMP®PRO9. To assess the effect of vaccination on ELISA detecting serum IgG against vaccine antigens, mixed general linear models were fitted to the data using JMP®PRO9. For all models described above, independent variables and their respective interactions were kept when $P<0.10$ in an attempt to reduce the type II error risk while maintaining a stringent type I error risk of 5%. The variable treatment was forced into all statistical models even in the absence of statistical significance. Age in days at enrollment, and BCS at enrollment were offered to all models.

Using the materials and methods described above in this example, the following results were obtained.

Descriptive statistics. Descriptive statistics regarding average age at enrollment (days), average BCS at enrollment and at 6±1 days postpartum, average gestation length at enrollment, and total number of animals enrolled are presented in Table 5. Only pregnant heifers were enrolled in this study, allowing us to have as little variation between animals as possible.

TABLE 5

Descriptive statistics of treatment groups

|  | Control | Vaccine 1 | Vaccine 2 | Vaccine 3 | Vaccine 4 | Vaccine 5 |
| --- | --- | --- | --- | --- | --- | --- |
| Average age (days) at enrollment (±SE) | 664 (3.72) | 655 (5.2) | 665 (5.24) | 669 (5.24) | 666 (5.24) | 668 (5.24) |

TABLE 5-continued

| | Descriptive statistics of treatment groups | | | | | |
|---|---|---|---|---|---|---|
| | Control | Vaccine 1 | Vaccine 2 | Vaccine 3 | Vaccine 4 | Vaccine 5 |
| Average body condition score at enrollment (±SE) | 3.71 (0.03) | 3.76 (0.05) | 3.74 (0.05) | 3.65 (0.05) | 3.72 (0.05) | 3.66 (0.05) |
| Average body condition score at 6 ± 1 (±SE) | 3.5 (0.02) | 3.49 (0.03) | 3.52 (0.03) | 3.49 (0.03) | 3.44 (0.03) | 3.50 (0.03) |
| Average days of gestation at enrollment (±SE) | 230 (0.21) | 230 (0.29) | 230 (0.29) | 230 (0.29) | 230 (0.29) | 230 (0.29) |
| Total enrolled animals | 105 | 54 | 53 | 53 | 53 | 53 |

Effect of vaccination on incidence of researcher diagnosed puerperal metritis (RDPMET), farm diagnosed puerperal metritis (FDPMET), and rectal temperature at 6±1 DIM. The effect of vaccination on the incidence of RDPMET is presented in Table 6. When evaluated separately, vaccines 1, 2 and 3 were associated with numerical reductions in the incidence of RDPMET, whereas vaccines 4 and 5 were associated with increased incidences. However, these differences were not statistically significant (P-value=0.21). When vaccines were evaluated grouped as either subcutaneous or intravaginal vaccines, the subcutaneous vaccines were associated with a significant reduction in the incidence of RDPMET (P-value=0.03).

TABLE 6

Effects of different vaccine formulations on incidence of researcher diagnosed puerperal metritis. Vaccines were evaluated separately in Model 1, and grouped in Model 2. Age in days and body condition score at enrollment were offered to both models

| Model and variables | Puerperal metritis incidence (%) | Coefficients (SE) | Odds ratio (95% CI) | P-value |
|---|---|---|---|---|
| Model 1 | | | | |
| Control | 12.12 | Ref. | baseline | 0.21 |
| Vaccine 1 | 6.25 | −0.14 (0.55) | 0.48 (0.13-1.80) | |
| Vaccine 2 | 4.08 | −0.59 (0.64) | 0.31 (0.07-1.44) | |
| Vaccine 3 | 2.04 | −1.30 (0.86) | 0.15 (0.02-1.20) | |
| Vaccine 4 | 13.46 | 0.70 (0.42) | 1.13 (0.41-3.01) | |
| Vaccine 5 | 14.00 | 0.75 (0.42) | 1.18 (0.43-3.21) | |
| Intercept | | −2.56 (0.25) | | |
| Model 2 | | | | |
| Control | 12.12 | Ref. | baseline | 0.03 |
| Subcutaneous | 4.11 | −0.83 (0.31) | 0.31 (0.11-0.86) | |
| Intravaginal | 13.73 | 0.48 (0.26) | 1.15 (0.50-2.63) | |
| Intercept | | −2.32 (0.20) | | |

The effect of vaccination on incidence of FDPMET is present in Table 7. When the vaccines were evaluated separately, the incidence of FDPMET tended to be different among the treatments (P-value=0.064). Additionally, when the vaccines were evaluated grouped as subcutaneous or intravaginal vaccines, the subcutaneous vaccines were associated with a significantly lower odds of FDPMET (P-value=0.047).

TABLE 7

Effects of different vaccine formulations on incidence of farm diagnosed puerperal metritis. Vaccines were evaluated separately in Model 1, and grouped in Model 2. Age in days and body condition score at enrollment were offered to both models

| Model and variables | Puerperal metritis incidence (%) | Coefficients (SE) | Odds ratio (95% CI) | P-value |
|---|---|---|---|---|
| Model 1 | | | | |
| Control | 27.62 | Ref. | baseline | 0.064 |
| Vaccine 1 | 11.11 | −0.73 (0.38) | 0.33 (0.13-0.85) | |
| Vaccine 2 | 16.98 | −0.24 (0.33) | 0.54 (0.23-1.23) | |
| Vaccine 3 | 20.75 | 0.005 (0.31) | 0.69 (0.31-1.51) | |
| Vaccine 4 | 33.96 | 0.68 (0.27) | 1.35 (0.66-2.74) | |
| Vaccine 5 | 19.23 | −0.09 (0.32) | 0.62 (0.28-1.40) | |
| Intercept | | −1.34 (0.14) | | |
| Model 2 | | | | |
| Control | 27.62 | Ref. | baseline | 0.047 |
| Subcutaneous | 16.25 | −0.43 (0.18) | 0.51 (0.28-0.93) | |
| Intravaginal | 26.67 | 0.19 (0.18) | 0.95 (0.52-1.75) | |
| Intercept | | −1.20 (0.12) | | |

Figure 3:
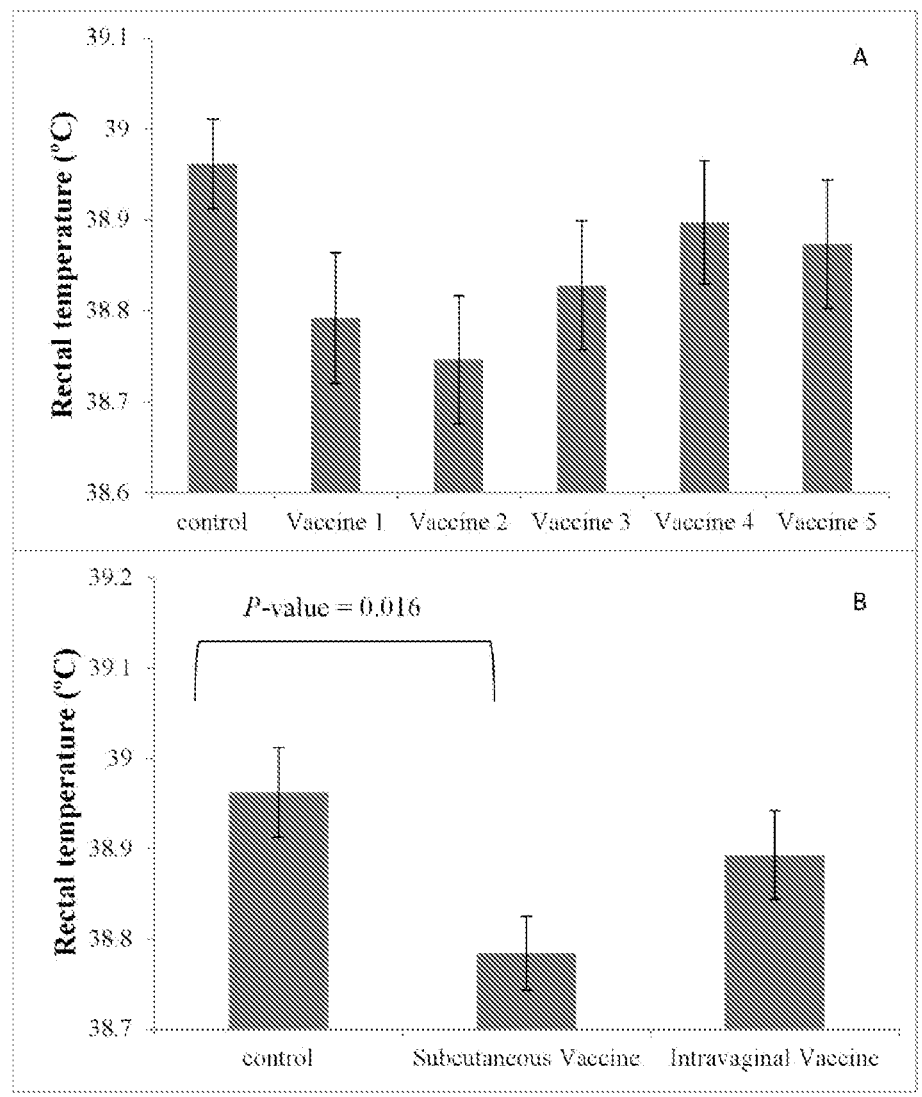
FIG. 3 shows an example of an effect of vaccination on rectal temperature at 6±1 DIM. Vaccines were evaluated separately (A, P-value=0.14), and grouped (B, P-value=0.018). Standard errors of the means are represented by the error bars.

The effect of vaccination on rectal temperature at 6±1 DIM is presented in FIG. 3. Rectal temperature was not statistically different among the treatment groups when the vaccines were evaluated separately (P-value=0.14). However, rectal temperature was statistically different between the treatment groups when the vaccines were evaluated grouped as control, subcutaneous vaccines or intravaginal vaccines (P-value=0.018). Subcutaneous vaccination was associated with a significant reduction in rectal temperature at 6±1 DIM.

Effect of vaccination on incidence of endometritis and uterine secretion culture outcomes. Vaccines were not effective in preventing endometritis, when evaluated separately or when grouped as subcutaneous and intravaginal vaccines (P-value=0.99). Endometritis incidence was 8.57%, 7.89%, 12.12%, 7.50%, 9.09%, and 9.76% for control, vaccine 1, vaccine 2, vaccine 3, vaccine 4, and vaccine 5, respectively. The incidence of endometritis was 9.01% and 9.46% for subcutaneous and intravaginal vaccines, respectively. Additionally, there was no significant effect of vaccination on the likelihood of intrauterine bacterial contamination (Table 8).

TABLE 8

Effects of different vaccine formulations on incidence of intrauterine
*Escherichia coli* at 2 ± 1 DIM, *Fusobacterium necrophorum*
at 6 ± 1 DIM and *Trueperella pyogenes* at 35 ± 3 DIM.
Vaccines were evaluated separately in Model 1, Model 3 and Model 5;
and grouped in Model 2, Model 4 and Model 6. Age in days and
body condition score at enrollment were offered to all models

| Model and variables | Cows positive for intrauterine culture (%) | Coefficients (SE) | Odds ratio (95% CI) | P-value |
|---|---|---|---|---|
| Model 1 | *E. coli* | | | |
| Control | 55.00 | Ref. | baseline | 0.63 |
| Vaccine 1 | 47.06 | −0.02 (0.25) | 0.75 (0.38-1.48) | |
| Vaccine 2 | 46.15 | −0.06 (0.25) | 0.72 (0.36-1.41) | |
| Vaccine 3 | 40.38 | −0.35 (0.26) | 0.54 (0.27-1.06) | |
| Vaccine 4 | 50.94 | 0.12 (0.25) | 0.86 (0.44-1.68) | |
| Vaccine 5 | 50.00 | 0.04 (0.26) | 0.80 (0.40-1.58) | |
| Intercept | | 1.96 (1.13) | | |
| Model 2 | *E. coli* | | | |
| Control | 55.00 | Ref. | baseline | 0.26 |
| Subcutaneous | 44.52 | −0.21 (0.14) | 0.66 (0.40-1.10) | |
| Intravaginal | 50.49 | 0.01 (0.16) | 0.83 (0.48-1.44) | |
| Intercept | | | | |
| Model 3 | *F. necrophorum* | | | |
| Control | 48.98 | Ref. | baseline | 0.76 |
| Vaccine 1 | 36.00 | −0.39 (0.26) | 0.59 (0.29-1.18) | |
| Vaccine 2 | 48.00 | 0.11 (0.26) | 0.96 (0.49-1.90) | |
| Vaccine 3 | 48.00 | 0.11 (0.26) | 0.96 (0.49-1.90) | |
| Vaccine 4 | 47.17 | 0.07 (0.25) | 0.93 (0.48-1.81) | |
| Vaccine 5 | 44.00 | −0.05 (0.26) | 0.82 (0.41-1.62) | |
| Intercept | | −0.19 (0.11) | | |
| Model 4 | *F. necrophorum* | | | |
| Control | 48.98 | Ref. | baseline | 0.74 |
| Subcutaneous | 44.00 | −0.09 (0.14) | 0.82 (0.49-1.36) | |
| Intravaginal | 45.63 | −0.02 (0.16) | 0.87 (0.50-1.52) | |
| Intercept | | −0.15 (0.11) | | |
| Model 5 | *T. pyogenes* | | | |
| Control | 14.49 | Ref. | baseline | 0.37 |
| Vaccine 1 | 5.26 | −0.80 (0.63) | 0.30 (0.06-1.46) | |
| Vaccine 2 | 21.21 | 0.77 (0.42) | 1.44 (0.48-4.32) | |
| Vaccine 3 | 12.50 | 0.05 (0.46) | 0.70 (0.21-2.30) | |
| Vaccine 4 | 12.12 | 0.06 (0.50) | 0.70 (0.20-2.52) | |
| Vaccine 5 | 7.32 | −0.49 (0.54) | 0.41 (0.10-1.61) | |
| Intercept | | −16.55 (5.48) | | |
| Model 6 | *T. pyogenes* | | | |
| Control | 14.49 | Ref. | baseline | 0.50 |
| Subcutaneous | 12.61 | 0.01 (0.26) | 0.74 (0.30-1.82) | |
| Intravaginal | 9.46 | −0.32 (0.31) | 0.53 (0.19-1.53) | |
| Intercept | | −16.66 (5.48) | | |

Effect of vaccination on reproduction. Cows that received subcutaneous vaccination were 1.36 times more likely to conceive when compared to control cows (P-value=0.04). However, for cows that received intravaginal vaccines, the likelihood of conceiving was not statistically different from control cows (Hazard ratio=1.12, P-value=0.46). Age in days at enrollment and BCS at enrollment were retained in the model for this analysis (P-value=0.02 and 0.01, respectively). The improvement in reproductive performance is further illustrated by survival analysis (FIG. 5) which demonstrates that cows vaccinated with subcutaneous vaccines became pregnant significantly faster than control cows and cows that received intravaginal vaccination.

Figure 4:
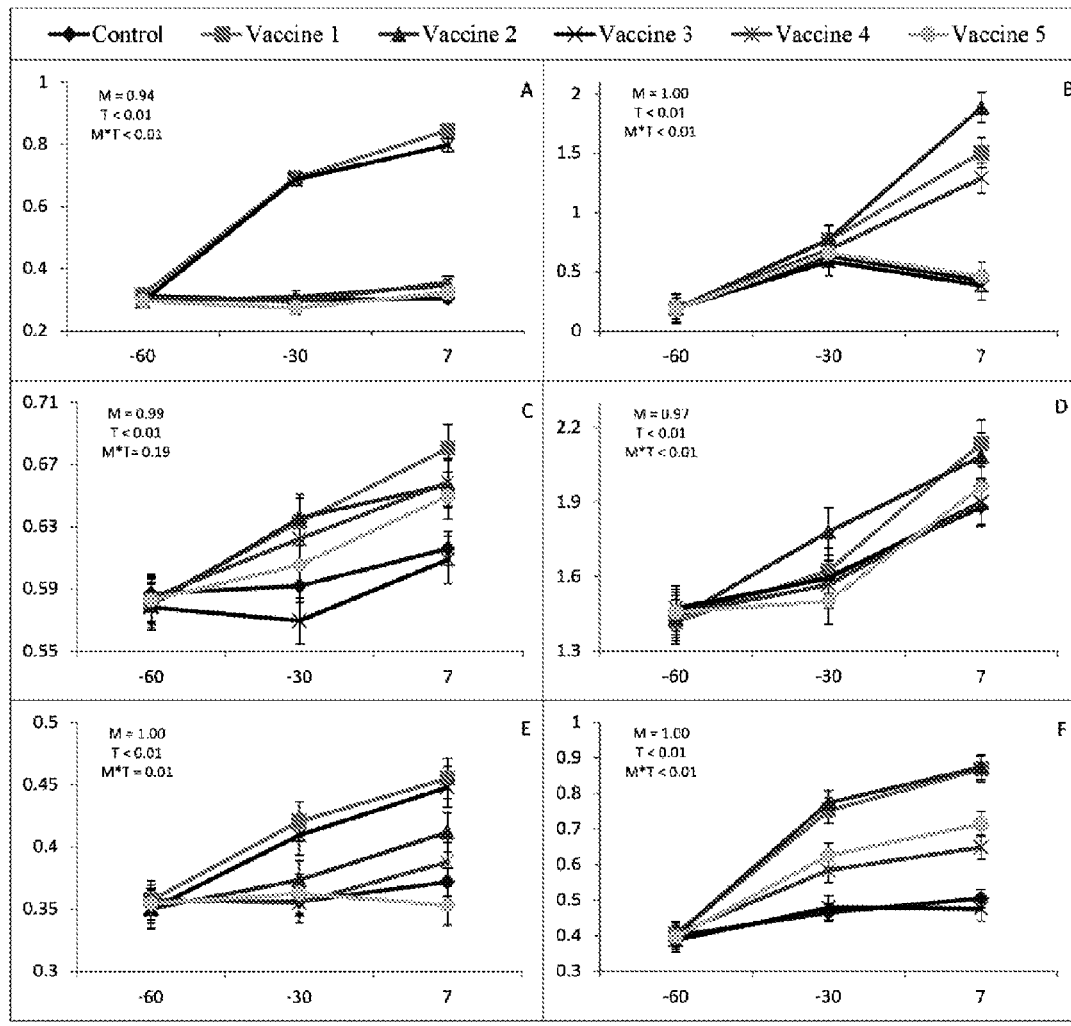
FIG. 4 shows an example of an effect of vaccination on ELISA-detected serum IgG against *E. coli* (A), FimH (B), *F. necrophorum* (C), LKT (D), *T. pyogenes* (E), and PLO (F). X-axis represents days relative to calving, while Y-axis represents $OD_{650}$ of ELISA-detected serum IgG against several antigens. Standard errors of the means are represented by the error bars.

Serological responses to vaccination. The effect of vaccination on ELISA-detected serum IgG against several antigens is presented in FIG. 4. In general, vaccination induced a significant increase in serum IgG titers against all antigens; subcutaneous vaccination was more effective at increasing serum IgG titers than intravaginal vaccination.

Figure 5:
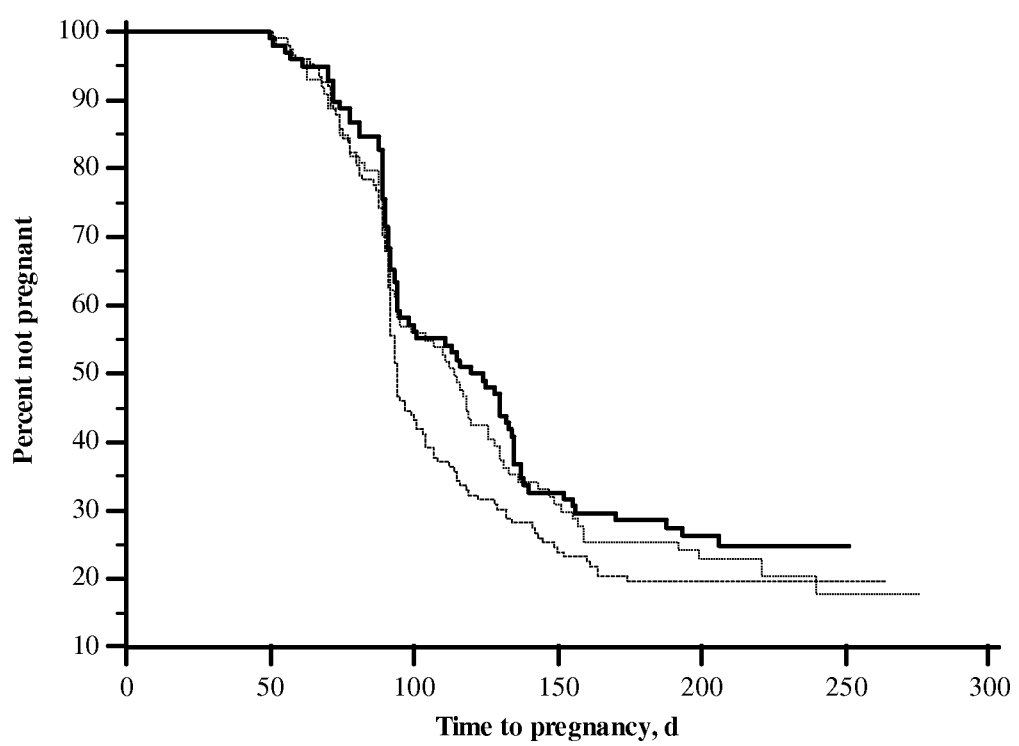
FIG. 5 shows an example of Kaplan-Meier survival analysis of calving-to-conception interval by treatment grouped as control, subcutaneous vaccines and intravaginal vaccines. The median calving-to-conception interval for subcutaneous vaccines (inner interrupted line), intravaginal vaccines (middle interrupted line), and control (solid line) was 94, 114, and 120 respectively. (P-value=0.04).

FIG. 5 shows an example of Kaplan-Meier survival analysis of calving-to-conception interval by treatment grouped as control, subcutaneous vaccines and intravaginal vaccines. The vaccination administrations were: control (no vaccine), subcutaneous vaccines (vaccines 1, 2, and 3 combined) and intravaginal vaccine (vaccines 4 and 5 combined). The Y axis is the % of cows not pregnant and the X axis is the days from parturition until pregnancy. The median calving-to-conception interval for subcutaneous vaccines (inner interrupted line), intravaginal vaccines (middle interrupted line), and control (solid line) was 94, 114, and 120 respectively. (P-value=0.04). The slope of the line representing the subcutaneous vaccine is steepest and demonstrates that an increased number of cows became pregnant in the subcutaneous vaccine group when compared to the intravaginal vaccine and control groups.

As will be apparent from the foregoing results presented in this Example, the effects of 5 different vaccine formulations (3 subcutaneous vaccines and 2 intravaginal vaccines) containing different combinations of proteins (FimH, *F. necrophorum* leukotoxin (LKT), *T. pyogenes* pyolysin (PLO) and inactivated whole cells (*E. coli*, *F. necrophorum* and *T. pyogenes*) on the uterine health of dairy cows are different in that subcutaneous vaccination significantly decreased the incidence of puerperal metritis, whereas intravaginal vaccination was not effective.

Puerperal metritis is characterized by inflammation of the entire thickness of the uterine walls, and is associated with signs of systemic illness such as dullness, decreased milk yield and fever. When diagnosed as described herein, puerperal metritis incidence was 12.12% and when diagnosed by farm workers it was 27.62%. This discrepancy can be attributed to the period during which the cows were monitored; whereas farm workers monitored the cows daily during their first 20 days after parturition, the research team examined the cows at 6±1 days after calving. Cows were examined at this time point because metritis peaks in the first 7 days after calving. However, in general, the effect of vaccination on puerperal metritis was consistent between the research group's and the farm workers' diagnoses; subcutaneous vaccination significantly lowered the incidence of puerperal metritis, whereas intravaginal vaccine was not effective in preventing the disease.

E. coli and F. necrophorum are gram-negative bacteria, characterized by the presence of lipopolysaccharide (LPS) in their outer membrane, and are known etiological agents of puerperal metritis; LPS is known to cause increased body temperature in cattle. Although vaccination did not significantly decrease the percentage of cows that were positive for intrauterine E. coli and F. necrophorum, subcutaneously vaccinated cows did have a lower rectal temperature at 6±1 DIM. This suggests that, even in the presence of bacteria in the uterus, immunized cows were less likely to develop systemic signs caused by LPS released from E. coli and F. necrophorum. It is known that reducing the bacterial load of E. coli decreases the severity of the disease; therefore, immunization decreased the pathogen-load inside the uterus.

Mucosal immune responses can be effectively induced by the administration of vaccines onto mucosal surfaces, whereas subcutaneous and intramuscular vaccines typically fail to induce mucosal immunity, and are less effective in preventing infection of mucosal surfaces. Promising results regarding prevention of human UTI by intravaginal immunization with a whole-cell vaccine have already been reported. However, it is not known how local synthesis of specific antibodies by uterine antibody-secreting cells contributes to uterine immunity. In the present study, intravaginal immunization was not effective in preventing uterine diseases.

In general, subcutaneous vaccination increased the serum levels of IgG against E. coli, FimH, F. necrophorum, LKT, T. pyogenes, and PLO.

It is known that F. necrophorum LKT is highly toxic to bovine PMNs, inducing apoptosis-mediated killing of them; this toxicity is dose-dependent. It is possible that immunizing the cows against LKT might have reduced the detrimental effect of this toxin on intrauterine PMNs, improving the ability of the innate immune system to eliminate bacterial infections from the uterus through phagocytosis. Recruited PMNs are key players in the immune defense of the uterus; reduced migration of PMNs 2 weeks before calving is associated with retained placenta, and lower phagocytic activity and oxidative burst capacity of PMNs are associated with occurrence of metritis and endometritis.

The incidence of puerperal metritis was significantly decreased with prepartum subcutaneous vaccination with vaccines containing different combinations of proteins (FimH, LKT, PLO) and inactivated whole cells (E. coli, F. necrophorum and T. pyogenes). In contrast, intravaginal vaccination was not effective in decreasing the incidence of puerperal metritis. Thus a commercially produced vaccine against metritis could become an integral part of a preventive strategy against metritis, which would be expected to reduce incidence of the disease and reduce use of antibiotics thereby alleviating both animal distress and the overall negative economic impact of metritis on the dairy industry.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A method of improving reproductive function of a ruminant comprising subcutaneously administering to the ruminant a veterinary composition comprising inactivated whole cells of *Escherichia coli* (*E. coli*), *Trueperella pyogenes* (*T. pyogenes*), *Fusobacterium necrophorum* (*F. necrophorum*), and *F. necrophorum* leukotoxin (LKT) protein, *E. coli* type 1 fimbrial adhesin (FimH) protein, and *T. pyogenes* pyolysin (PLO) protein, such that the reproductive function of the ruminant is improved, wherein the improving the reproductive function of the ruminant comprises reducing a calving-to-conception interval relative to a calving-to-conception interval of a control, wherein the control is a calving-to-conception interval from a ruminant that received an intravaginal administration of the veterinary composition.

2. The method of claim 1, wherein the ruminant is a cow.

* * * * *

SEQUENCE LISTING

<160> NUMBER OF SEQ ID NOS: 14

<210> SEQ ID NO 1
<211> LENGTH: 21
<212> TYPE: DNA
<213> ORGANISM: artificial sequence
<220> FEATURE:
<223> OTHER INFORMATION: PCR primer

<400> SEQUENCE: 1
tcatcaacaa tccacgaaga g                          21

<210> SEQ ID NO 2
<211> LENGTH: 20
<212> TYPE: DNA
<213> ORGANISM: artificial sequence
<220> FEATURE:
<223> OTHER INFORMATION: PCR primer

<400> SEQUENCE: 2
ttgcctccag ttgacgcttt                            20

<210> SEQ ID NO 3
<211> LENGTH: 24
<212> TYPE: DNA
<213> ORGANISM: artificial sequence
<220> FEATURE:

```
<223> OTHER INFORMATION: PCR primer

<400> SEQUENCE: 3
gcagggttgg tgaaagagtt tact                                            24

<210> SEQ ID NO 4
<211> LENGTH: 26
<212> TYPE: DNA
<213> ORGANISM: artificial sequence
<220> FEATURE:
<223> OTHER INFORMATION: PCR primer

<400> SEQUENCE: 4
gcttgatata accttcagaa tttgca                                          26

<210> SEQ ID NO 5
<211> LENGTH: 22
<212> TYPE: DNA
<213> ORGANISM: artificial sequence
<220> FEATURE:
<223> OTHER INFORMATION: PCR primer

<400> SEQUENCE: 5
cactacgctc accattcaca ag                                              22

<210> SEQ ID NO 6
<211> LENGTH: 22
<212> TYPE: DNA
<213> ORGANISM: artificial sequence
<220> FEATURE:
<223> OTHER INFORMATION: PCR primer

<400> SEQUENCE: 6
gctgtaatcc gctttgtctg tg                                              22

<210> SEQ ID NO 7
<211> LENGTH: 21
<212> TYPE: DNA
<213> ORGANISM: artificial sequence
<220> FEATURE:
<223> OTHER INFORMATION: PCR primer

<400> SEQUENCE: 7
tgcagaacgg ataagccgtg g                                               21

<210> SEQ ID NO 8
<211> LENGTH: 21
<212> TYPE: DNA
<213> ORGANISM: artificial sequence
<220> FEATURE:
<223> OTHER INFORMATION: PCR primer

<400> SEQUENCE: 8
tgcagaacgg ataagccgtg g                                               21

<210> SEQ ID NO 9
<211> LENGTH: 20
<212> TYPE: DNA
<213> ORGANISM: artificial sequence
<220> FEATURE:
<223> OTHER INFORMATION: PCR primer

<400> SEQUENCE: 9
aatcggagta gtaggttctg                                                 20
```

```
<210> SEQ ID NO 10
<211> LENGTH: 18
<212> TYPE: DNA
<213> ORGANISM: artificial sequence
<220> FEATURE:
<223> OTHER INFORMATION: PCR primer

<400> SEQUENCE: 10
tttggtaact gccactgc                                                 18

<210> SEQ ID NO 11
<211> LENGTH: 30
<212> TYPE: DNA
<213> ORGANISM: artificial sequence
<220> FEATURE:
<223> OTHER INFORMATION: PCR primer

<400> SEQUENCE: 11
acagcatcct cgagtgccgg attgggaaac                                    30

<210> SEQ ID NO 12
<211> LENGTH: 26
<212> TYPE: DNA
<213> ORGANISM: artificial sequence
<220> FEATURE:
<223> OTHER INFORMATION: PCR primer

<400> SEQUENCE: 12
tggaattccc taggatttga cattgt                                        26

<210> SEQ ID NO 13
<211> LENGTH: 30
<212> TYPE: DNA
<213> ORGANISM: artificial sequence
<220> FEATURE:
<223> OTHER INFORMATION: PCR primer

<400> SEQUENCE: 13
cgcggatcca tgaaacgtgt tattaccctg                                    30

<210> SEQ ID NO 14
<211> LENGTH: 48
<212> TYPE: DNA
<213> ORGANISM: artificial sequence
<220> FEATURE:
<223> OTHER INFORMATION: PCR primer

<400> SEQUENCE: 14
cccaagcttc tagtgatggt gatggtgatg gccgccagta ggcaccac                48
```